United States Patent [19]
Carter et al.

[11] Patent Number: 6,107,302
[45] Date of Patent: Aug. 22, 2000

[54] GUANINE DERIVATIVE

[75] Inventors: Barry Howard Carter, Kinston; Jane Muse Partin, Raleigh; Peter Gregory Varlashkin, Clayton; Richard Augustus Winnike, Durham, all of N.C.; William Bayne Grubb, III, Athens, Ga.; Gregory Alan Conway, Greenville, S.C.; Philip George Lake, Dartford, United Kingdom; David Michael Skinner, Dartford, United Kingdom; David James Whatrup, Dartford, United Kingdom

[73] Assignee: Glaxo Wellcome Inc., Research Triangle Park, N.C.

[21] Appl. No.: 08/875,173

[22] PCT Filed: Jan. 19, 1996

[86] PCT No.: PCT/GB96/00117

§ 371 Date: Sep. 22, 1997

§ 102(e) Date: Sep. 22, 1997

[87] PCT Pub. No.: WO96/22291

PCT Pub. Date: Jul. 25, 1996

[30] Foreign Application Priority Data

Jan. 20, 1995 [GB] United Kingdom .................. 9501178

[51] Int. Cl.$^7$ ................. A01N 43/90; C07F 5/02; C07F 9/02; C07D 473/00
[52] U.S. Cl. ................. 514/262; 544/267; 544/276; 544/277; 544/229; 544/244
[58] Field of Search ............. 514/262; 544/267, 544/276, 277, 229, 244

[56] References Cited

FOREIGN PATENT DOCUMENTS

| 0 308 065 | 3/1989 | European Pat. Off. . |
| 0 596 542 | 5/1994 | European Pat. Off. . |
| 94 29311 | 12/1994 | WIPO . |

OTHER PUBLICATIONS

Antiviral Chemistry & Chemotherapy, vol. 3, No. 3. 1992, pp. 157–164 XP002000503 Beauchamp et al p. 162 left hand column.

Antiviral Chemistry & Chemotherapy (1992) 3(3), 157–164 Beauchamp et al "Amino acid ester prodrugs of acyclovir".

*Primary Examiner*—Russell Travers
*Attorney, Agent, or Firm*—Nixon & Vanderhye

[57] ABSTRACT

The invention relates to an anhydrous crystalline form of (2-[2-amino-1,6-dihydro-6-oxo-purin-9-yl)methoxy]ethyl L-valinate hydrochloride (otherwise known as valaciclovir hydrochloride) and a process for preparing it.

9 Claims, 4 Drawing Sheets

GUANINE DERIVATIVE

This Application is a 371 of PCT/GB96/00117 filed Jan. 19, 1996, which claims Provisional British Application 9501178.9 filed Jan. 20, 1995.

The present invention relates to a specific crystalline form of the antiviral compound valaciclovir hydrochloride, and to a process for producing it.

The compound 9-[(2-hydroxyethoxy)methyl]guanine, otherwise known as acyclovir possesses potent antiviral activity and is widely used in the treatment and prophylaxis of viral infections in humans, particularly infections caused by the herpes group of viruses (see, for example, Schaeffer et al, Nature, 272, 583–585 (1978), UK patent no. 1,523,865 and U.S. Pat. No. 4,199,574). However, acyclovir is poorly absorbed from the gastrointestinal tract upon oral administration and this low bioavailability means that multiple high doses of oral drug may need to be administered, especially for the treatment of less sensitive viruses or infections in order to achieve and maintain effective anti-viral levels in the plasma.

The L-valine ester of acyclovir, namely (2-[2-amino-1, 6-dihydro-6-oxo-purin-9-yl)methoxyethyl L-valinate, (otherwise known as valaciclovir) has been shown to possess much improved bioavailability whilst retaining the anti-viral properties of acyclovir. A preferred form of this compound is its hydrochloride salt which is otherwise known as valaciclovir hydrochloride. The L-valinate ester of acyclovir and its salts including the hydrochloride salt are disclosed in U.S. Pat. No. 4,957,924 (see particularly example IB), European Pat. No. 0308,065 (see particularly example IB) and Beauchamp et al, Antiviral Chemistry and Chemotherapy, 3(3), 157–164 (1992) (see particularly page 162 column 1).

We have now found that valaciclovir hydrochloride can exist in various forms, and moreover we have discovered a form of valaciclovir hydrochloride which is anhydrous and crystalline and which surprisingly has particularly good pharmaceutical properties. It is particularly stable and essentially non-hygroscopic. Batches of this crystalline form can be consistently made to a high crystal form purity i.e. where the proportion of other amorphous and crystalline forms of valaciclovir hydrochloride is limited. Furthermore this anhydrous crystalline form has good storage properties and can be readily formulated into pharmaceutical compositions such as tablets and capsules.

Accordingly in a first aspect of the invention there is provided valaciclovir hydrochloride in anhydrous crystalline form including the following d spacing pattern (in Angstroms):

10.20 ±0.08, 8.10±0.06, 7.27±0.06, 6.08±0.05, 5.83±0.03, 5.37±0.02, 5.23±0.02, 4.89±0.02, 4.42±0.02, 4.06±0.02, 3.71±0.02, 3.39±0.02, 3.32±0.02, 2.91±0.02, 2.77±, 0.02.

Figure 1:
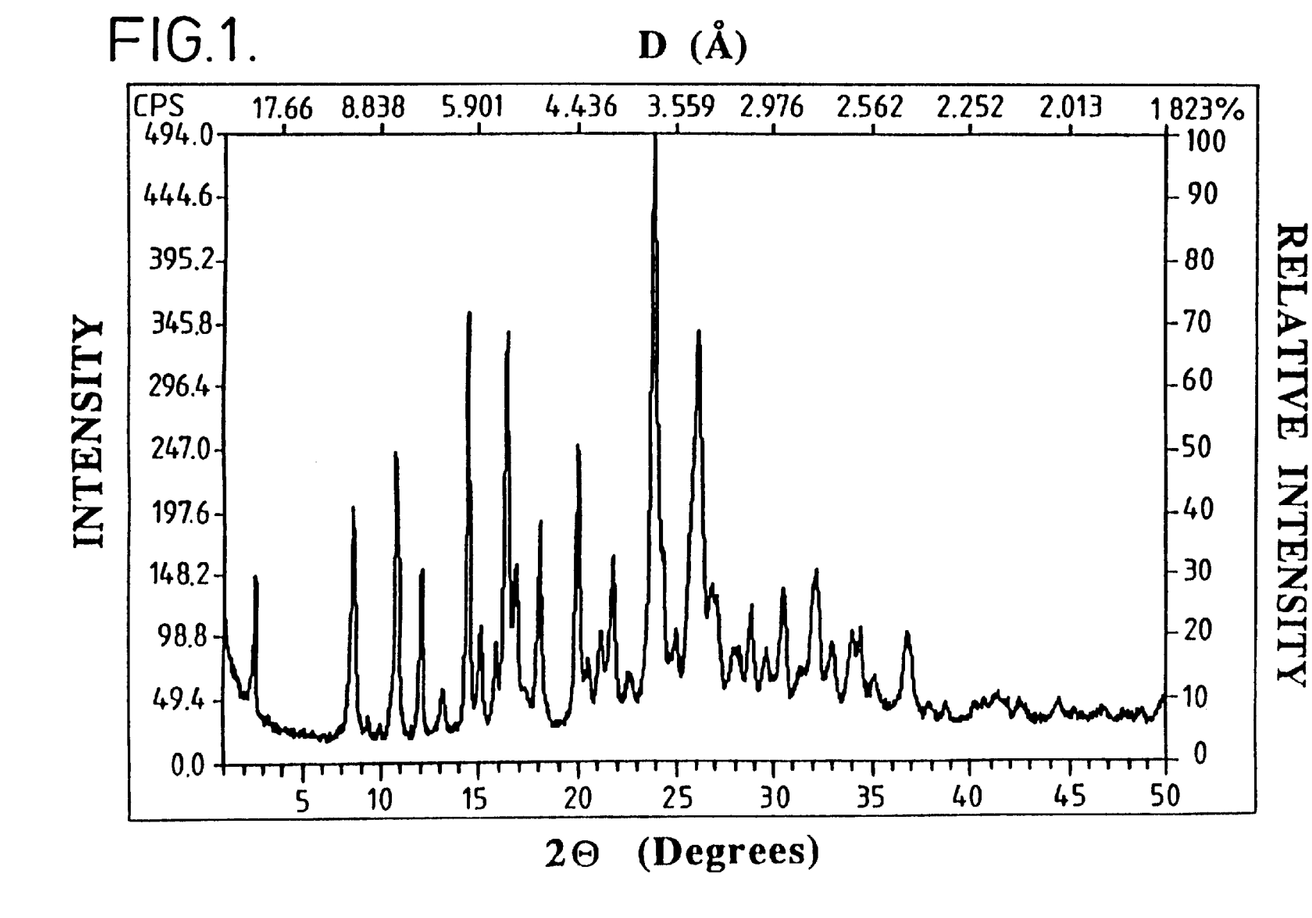
Figure 2:
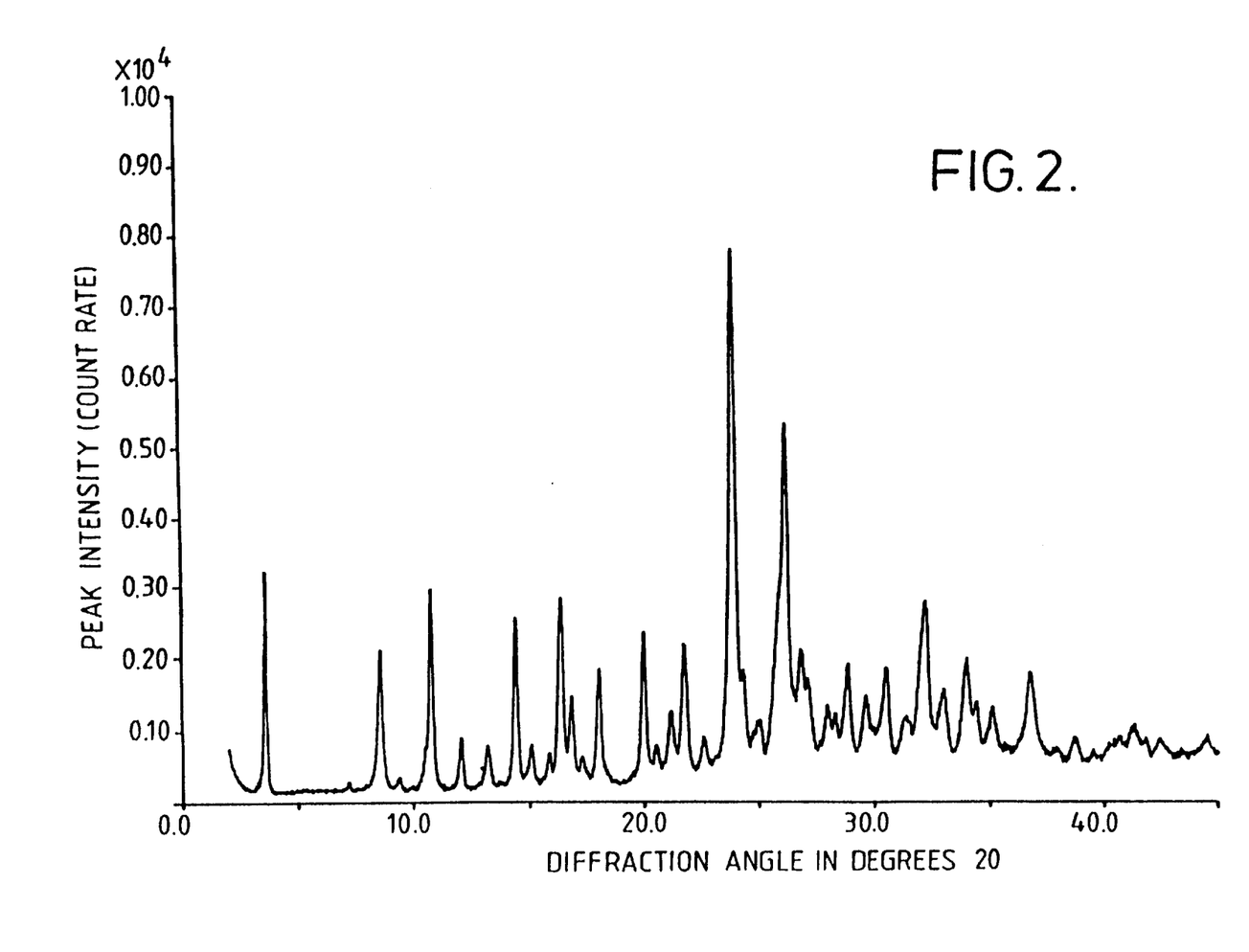
Figure 3:
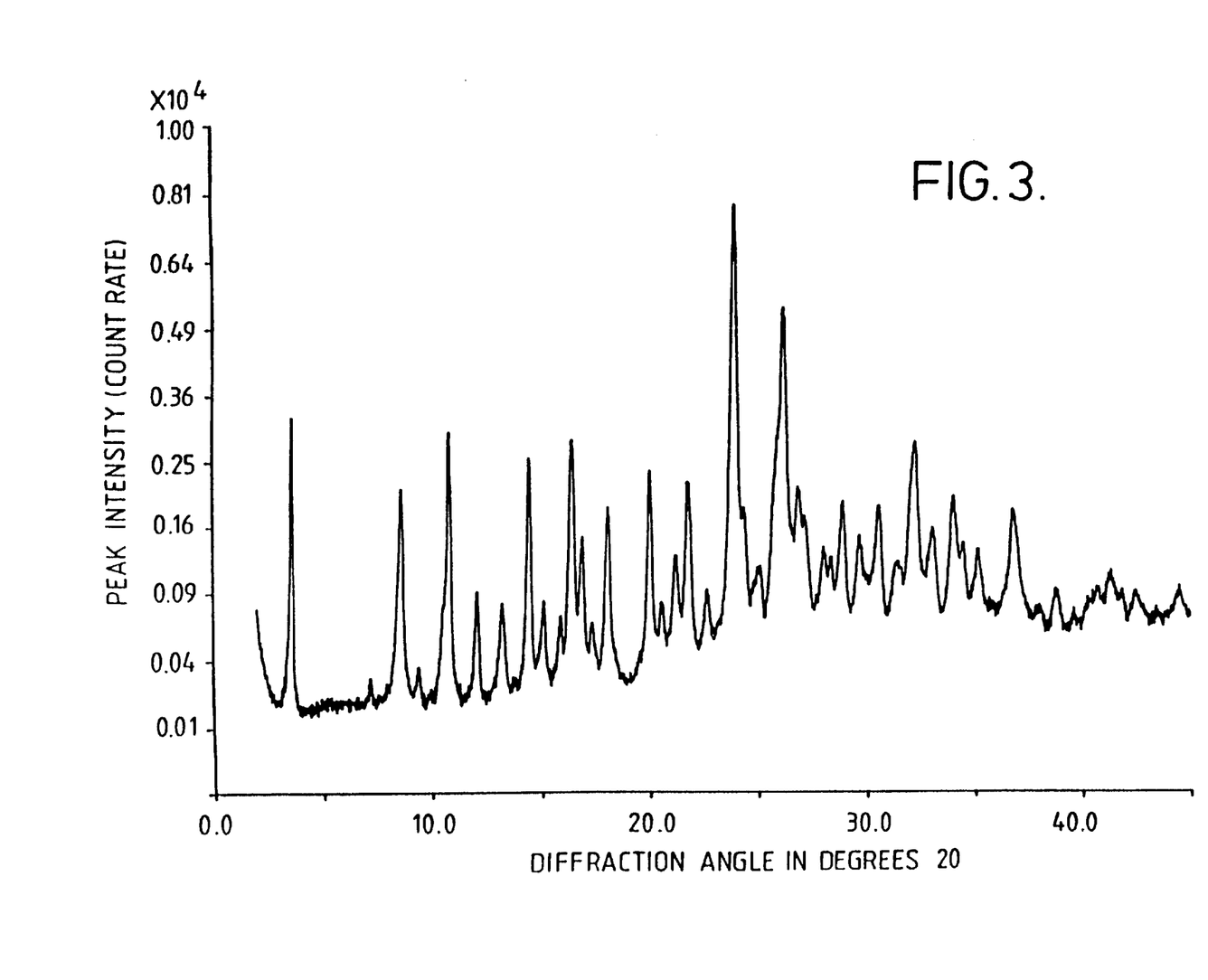

Hereinafter by "anhydrous crystalline form" according to the invention, we mean a crystalline form having substantially the same X-ray powder diffraction pattern as shown in FIGS. 1 to 3, or having substantially the same d spacing pattern as defined above.

Any particular crystalline form of a molecule will have its own unique d spacing pattern which can be determined from its powder X-ray diffraction pattern using the Bragg equation $$n\lambda = 2d \sin \Theta$$

where: n is the order of diffraction (usually 1);
$\lambda$ is the wavelength of the radiation;
d is the d spacing (Angstroms); and
$\Theta$ is the angle of deflection of the radiation It will be appreciated that the measured d spacings can vary slightly e.g. depending on the degree to which the powder sample is packed.

The invention relates to the anhydrous crystalline form both in pure form and in admixture with other forms of valaciclovir hydrochloride such as hydrated crystalline forms. For example in any batch containing the anhydrous crystalline valaciclovir hydrochloride, there may also be hydrated crystalline forms of the compound. Preferably the crystal form purity in any drug batch of valaciclovir hydrochloride is at least 70% w/w, more preferably at least 80% w/w, more preferably still at least 90% w/w, and most preferably at least 95% of anhydrous crystalline valaciclovir hydrochloride (as defined above).

In an alternative method of determining crystal form purity, since the anhydrous crystalline form of valaciclovir hydrochloride is essentially free of water of hydration, the proportion of hydrate forms of valaciclovir hydrochloride in any batch of the compound can be measured by the overall water of hydration content of each batch.

Accordingly in a second aspect of the invention there is provided valaciclovir hydrochloride having a water of hydration content of not more than 3% by weight (w/w) and including substantially the X-ray powder diffraction patterns of FIGS. 1 to 3, or substantially the same d spacing pattern shown above.

More preferably the water of hydration content is not more than 2% w/w, still more preferably not more than 1.5% w/w, and more preferably still not more than 1% w/w, and most preferably not more than 0.5% w/w.

This water of hydration content is measured by the Karl Fischer method which is well known in the art and is described in the 1990 U.S. Pharmacopoeia at pages 1619–1621, and the European Pharmacopoeia, second edition (1992), part 2, sixteenth fascicule at v. 3.5.6-1.

According to a further aspect, the present invention provides a process for the production of valaciclovir hydrochloride in anhydrous crystalline form which comprises treating valaciclovir hydrochloride with a solubilising solvent serving to convert an amount of valaciclovir hydrochloride into said anhydrous crystalline form having the d spacing pattern shown above in the first aspect of invention; and thereafter isolating said anhydrous crystalline form.

The invention also provides a process for the production of valaciclovir hydrochloride in an anhydrous crystalline form having the d spacings shown above, said process comprising the steps of.

a) forming valaciclovir in solution either in free base or salt form;

b) converting said free base valaciclovir or a salt thereof (when not the hydrochloride salt) to valaciclovir hydrochloride;

c) isolating valaciclovir hydrochloride from the solution and optionally removing unbound (damp, non-solvated) solvent leaving the valaciclovir hydrochloride in substantially dry form;

d) treating valaciclovir hydrochloride with a solubilising solvent serving to convert an amount of the optionally dried valaciclovir hydrochloride from step c) into said anhydrous crystalline form; and e) isolating said anhydrous crystalline form.

Valaciclovir may be prepared by any method known in the art, but preferably by the methods described in the references mentioned above (U.S. Pat. No. 4,957,924, European patent no. 0308,065, and Beauchamp et al, Antiviral Chemistry & Chemotherapy 303, 157–164 (1992), the disclosure of U.S. Pat. No. 4,957,924 being incorporated herein by reference). Preferably the process starts from acyclovir whose synthesis is described in Schaeffer et al, Nature, 272, 583–585 (1978), UK patent no. 1,523,865 and U.S. Pat. No. 4,199,574). Acyclovir is firstly esterified to its L-valine ester (valaciclovir), using an optionally protected L-valine for example carbobenzyloxy-L-valine (CBZ-L-valine) in a solvent such as pyridine or DMF in the presence of a coupling agent such as N,N'-dicyclohexylcarbodiimide, optionally in the presence of a base such as 4-dimethylaminopyridine as catalyst. Protecting groups can be removed in known manner (such as by treating with formic acid in the presence of 5% palladium on carbon) following the esterification reaction. Valaciclovir in the form of the free base or a salt of another acid (e.g. the formate) can be converted into the hydrochloride salt in conventional manner, for example by treatment with hydrochloric acid in a solvent. The synthesis of valaciclovir hydrochloride generally leads to the formation of the compound in solution in the reaction mixture from which it may be separated and purified as a solid product. The valaciclovir hydrochloride may then optionally be dried such as by slurrying in acetone and then drying. A number of factors influence the crystalline form of the solid product and in accordance with the present invention the conditions of separation and/or subsequent processing are adjusted to produce valaciclovir hydrochloride as the anhydrous crystalline form. For example a hydrate form of valaciclovir hydrochloride can be converted to the anhydrous crystalline form using a suitable solvent under appropriate conditions.

Such suitable solvent which is preferably a water-soluble organic solvent, should be sufficiently solubilising and be employed in an amount to allow partial solubilisation to effect the conversion and precipitation for example from hydrated crystalline form to the desired anhydrous crystalline form of valaciclovir hydrochloride. Advantageously the solvent is eventually removed by drying under vacuum. Preferably the organic solvent is an alcohol advantageously a lower alcohol containing 1 to 4 carbon atoms or a lower ketone (containing 3 to 6 carbon atoms). Most preferably the lower alcohol is ethanol or a solvent composed substantially of ethanol, for example in the form of denatured alcohol such as SVM or industrial methylated spirits. Most preferably also, the lower ketone contains water, preferably aqueous acetone such as having a water content of about 6% to about 12% by weight. Preferably the drug is slurried in the lower ketone. Our early investigations also suggest that methanol and isopropyl alcohol should also be suitable lower alcohols.

According to one particular embodiment of the invention, valaciclovir hydrochloride is formed in solution, for example in ethanol/water, obtained for example by the general method referred to above and the valaciclovir hydrochloride is isolated by partial removal of the solvent by distillation followed by precipitation, for example by addition of acetone. The valaciclovir hydrochloride (such as that isolated after step c above) can be separated at this stage in an unstable solvated form by filtration. This product which is in nondesired form can then optionally be dried and processed to the desired anhydrous crystalline form as described below.

The damp valaciclovir hydrochloride following the first isolation (as in step c above) is preferably dried; such as by being slurried in acetone then filtered and the damp solid dried for example about 30° to about 70° C. to provide substantially dry valaciclovir hydrochloride. At this point, the valaciclovir hydrochloride may contain a high proportion of the dehydrate form which has a theoretical water of hydration content of about 9.8%.

According to a process for forming anhydrous crystalline valaciclovir hydrochloride, the substantially dry valaciclovir hydrochloride (as obtained above) is mixed with an amount of lower alcohol such as ethanol or denatured alcohol, preferably in an amount of about 15% to 40% w/w, more preferably about 17% to 30% w/w. The mixture is then heated for example from about 50° C. to 70° C. for several hours. Finally the product is dried under vacuum to remove residual solvent, for example at about 50° C. to 70° C.

The present invention also provides the anhydrous crystalline form of valaciclovir hydrochloride (hereinafter identified as "the active compound") for use in medical therapy, e.g. in the treatment of a viral disease in an animal, e.g. a mammal such as a human. The compound is especially useful for the treatment of diseases caused by various DNA viruses, such as herpes infections, for example, herpes simplex I and 2, varicella zoster, cytomegalovirus, Epstein-Barr viruses or human herpes virus-6 (HHV-6) as well as diseases caused by hepatitis B. The active compound can also be used for the treatment of papilloma or wart virus infections and, may furthermore be administered in combination with other therapeutic agents, for example with zidovudine, to treat retroviral associated infections in particular HIV infections.

In addition to its use in human medical therapy, the active compound can be administered to other animals for treatment of viral diseases, e.g. to other mammals.

The present invention also provides a method for the treatment of a viral infection, particularly a herpes viral disease, in an animal, e.g. a mammal such as a human, which comprises administering to the animal an effective antiviral amount of the active compound.

The present invention also provides the use of the active compound in the preparation of a medicament for the treatment of a viral infection.

The active compound may be administered by any route appropriate to the condition to be treated, but the preferred route of administration is oral. It will be appreciated however, that the preferred route may vary with for example the condition of the recipient.

For each of the above-indicated utilities and indications the amounts required of the active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose win be in the range 1 to 150 mg per kilogram bodyweight of recipient per day, preferably in the range 5 to 320 mg per kilogram bodyweight per day (Unless otherwise indicated, all weights of the active ingredient are calculated with respect to the free base valaciclovir). The desired dose is preferably presented as one, two, three or four or more subdoses administered at appropriate intervals throughout the day. These sub-doses may be administered in unit dosage forms, for example, containing about 50 to 2000 mg, preferably about 250, 500, 1000 or 2000 mg of active ingredient per unit dose form.

The following dosage regimes are given for guidance:
   treatment of herpes simplex virus types 1 and 2 infection:
      total daily dose off about 1 or 2 g administered at 500 mg twice a day or 1 g twice a day for 5 to 10 days;
      suppression of herpes simplex virus types I and 2 infections: total daily dose about 250 to 1 g for about one to ten years (depending on the patient);

treatment of varicella zoster virus infections (for example shingles): total daily dose about 3 g administered at 1 g three times a day for seven days; suppression of cytomegalovirus infections: total daily dose about 8 g administered at 2 g 4 times a day; for transplant patients this daily dose is administered for three to six months for the period at risk; and for HIV positive patients a daily dose is administered as usually indicated for improving quality of lie, for example for two years or more.

Early results now indicate that valaciclovir can be used in the effective suppression or recurrent genital herpes at a once daily dose of from about 200 mg to about 1000 mg for an effective treatment period. The most likely daily dosages are 250 mg, 500 mg or 1000 mg.

While it is possible for the active ingredient to the administered alone, it is to present it as a pharmaceutical formulation. The formulation comprises the active ingredient as above defined, together with one or more pharmaceutically acceptable excipients therefor and optionally other therapeutic ingredients. The excipient(s) must be "acceptable" in the sense of being compatible with the other ingredients of the formulation and not deleterious to the recipient thereof.

The formulations include those suitable for oral administration and may conveniently be presented in unit dosage form prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets, sachets of granules or tablets (such as a swallowable, dispersible or chewable tablet) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Preferred unit dosage formulations are those containing a daily dose or unit daily sub-dose (as herein above recited) or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavouring agents or taste masking agents.

The invention is illustrated by the following examples:

EXAMPLE 1

A. 2-[(2-amino-1,6-dihydro-6-oxo-9H-purin-9-yl) methoxy]ethyl-N-[(benzoloxy)carbonyl]-L-valinate CBZ-L-valine (170 g) was dissolved in dimethylformamide (DMF) (750 ml) and cooled. A cold solution of N,N-dicyclohexyl-carbodiimide (DCC) (156.7 g) in DMF (266 ml) was added and stirred with cooling. Acyclovir (10.1 g) was added in a single portion, and then 4-(dimethylamino)pyridine (9.4 g) was added while maintaining cooling. The mixture was stirred cold overnight. A white precipitate of the by-product was then removed by filtration. The filtrate was reduced in volume by vacuum distillation and the concentrate treated with water (663 ml) then heated to 70° C. The suspension was cooled to 20° C., filtered and the solid washed with water.

The damp, crude material was then purified by recrystallisation from denatured alcohol (1.2 litres) to afford the title compound as a damp white crystalline solid (281.5 g).

B. 2-[(2-amino-1,6-dihydro-6-oxo-9H-purin-9-yl) methoxy]ethyl-L-valinate hydrochloride 2-[(2-amino-1,6-dihydro-6-oxo-9H-purin-9-yl)methoxy] ethyl-N-[(benzyloxy)carbonyl]-L-valinate (175 g) was charged to aqueous denatured alcohol (335 ml/795 ml) and heated to reflux. The solution was then cooled to 40° C. The suspension was treated with 5% palladium on carbon catalyst (35 g wet weight 50% wet with water) then formic acid (30.6 ml of 90% w/w) added over 1 hour. The reaction mixture was stirred for a further 1 hour then a second charge of formic acid made (19.5 ml) and the mixture filtered to remove the catalyst. The filter cake was washed with denatured alcohol and the combined filtrates were treated with concentrated hydrochloric acid (33.7 ml) and the resultant mixture was concentrated by vacuum distillation.

Acetone (1295 ml) was then added over 15 minutes and the suspension stirred for 1 hour before filtering off the product. The solid was then slurried with acetone (circa. 530 ml), refiltered and dried at 60° C. in vacuo to give the title compound (1123 g: 81.6%).

A 15 g sample of this material was combined with denatured alcohol (circa. 7 ml), to moisten and was heated with agitation at 60° C. overnight in a closed flask to avoid loss of alcohol and maintain the dampness of the mixture. The mixture was then dried at 60° C. in vacuo to afford the product as the desired morphic form.

Physical Data:

Karl Fischer value: 0.9% w/w water.

The X-ray powder diffraction patterns of the product of example 1B are shown in FIG. 1 of the accompanying drawings.

The d spacings and further X-ray diffraction data are shown in Table 1.

TABLE 1

| Peak No: | Angle (degrees) | Peak (counts) | d Spacing pattern (Å) | Error in d (± Å) | I/Imax (%) |
|---|---|---|---|---|---|
| 1 | 3.56 | 680 | 24.8 | 0.5 | 24 |
| 2 | 8.62 | 1151 | 10.25 | 0.08 | 39 |
| 3 | 9.42 | 87 | 9.38 | 0.07 | 3 |
| 4 | 10.86 | 1438 | 8.14 | 0.06 | 49 |

TABLE 1-continued

| Peak No: | Angle (degrees) | Peak (counts) | d Spacing pattern (Å) | Error in d (± Å) | I/Imax (%) |
|---|---|---|---|---|---|
| 5 | 12.10 | 835 | 7.31 | 0.06 | 28 |
| 6 | 13.22 | 198 | 6.69 | 0.05 | 6 |
| 7 | 14.49 | 2172 | 6.41 | 0.05 | 75 |
| 8 | 15.12 | 455 | 5.85 | 0.03 | 15 |
| 9 | 15.90 | 352 | 5.57 | 0.02 | 12 |
| 10 | 16.45 | 1969 | 5.38 | 0.02 | 68 |
| 11 | 16.90 | 744 | 5.24 | 0.02 | 25 |
| 12 | 17.33 | 119 | 5.11 | 0.02 | 4 |
| 13 | 18.12 | 1013 | 4.89 | 0.02 | 35 |
| 14 | 22.71 | 1429 | 4.43 | 0.02 | 49 |
| 15 | 20.55 | 256 | 4.32 | 0.02 | 8 |
| 16 | 21.21 | 370 | 4.19 | 0.02 | 12 |
| 17 | 21.83 | 753 | 4.07 | 0.02 | 26 |
| 18 | 22.71 | 95 | 3.91 | 0.02 | 3 |
| 19 | 23.95 | 2893 | 3.71 | 0.02 | 100 |
| 20 | 25.10 | 171 | 3.54 | 0.02 | 5 |
| 21 | 26.21 | 1784 | 3.40 | 0.02 | 61 |
| 22 | 26.89 | 428 | 3.31 | 0.02 | 14 |
| 23 | 27.08 | 373 | 3.29 | 0.02 | 12 |
| 24 | 28.02 | 158 | 3.18 | 0.02 | 5 |
| 25 | 28.27 | 161 | 3.15 | 0.02 | 5 |
| 26 | 28.91 | 391 | 3.09 | 0.02 | 13 |
| 27 | 29.68 | 191 | 3.01 | 0.02 | 6 |
| 28 | 30.55 | 502 | 2.92 | 0.02 | 17 |
| 29 | 31.34 | 110 | 2.85 | 0.02 | 3 |
| 30 | 31.58 | 98 | 2.83 | 0.02 | 3 |
| 31 | 32.13 | 597 | 2.78 | 0.02 | 20 |
| 32 | 32.96 | 260 | 2.72 | 0.02 | 8 |
| 33 | 33.99 | 344 | 2.64 | 0.02 | 11 |
| 34 | 34.38 | 374 | 2.61 | 0.02 | 12 |
| 35 | 35.12 | 141 | 2.55 | 0.02 | 4 |
| 36 | 36.78 | 408 | 2.44 | 0.02 | 14 |
| 37 | 38.71 | 101 | 2.32 | 0.02 | 3 |

I/Imax = (peak height/max. peak ht) × 100

The powder sample used to produce the above X-ray diffraction data was prepared by an equivalent method as the powder sample used to produce the X-ray diffraction date of table 2 described hereinafter) except that for the above data the following preparation was used to prepare the powder sample.

The sample was prepared by milling 1 g of sample in a plastic cup using two acrylic balls for 5 minutes with a Chemplex Spectromill. The samples were then back packed against a glass slide to a depth of 2 mm.

The X-ray diffraction scan was obtained using a Scintag PADV diffractometer in the step scan mode at 0.02° per step and a 10 second count per step. The sample holder was spun at 1 rotation per second during the scan. Additional setting as described below.

X-ray generator: 45 kV, 40 mA

Radiation: Copper K alpha radiation

Fixed divergent slit: 1 mm

Incident scatter slit: 2 mm

Diffracted scatter slit: 0.5 mm

Receiving slit: 0.3 mm

Goniometer radius: 235 mm

Detector: Scintillation with a graphite monochromator.

The peak intensities are reported as absolute counts of the peak top. The intensity units on the X-ray diffraction plot are counts/sec. The absolute counts=counts/sec×count time= counts/sec×10 sec. The peak intensities in the table have been corrected for background and copper K alpha II X-ray wavelength contribution.

Slight variations in d spacings are expected based on the specific diffractometer employed and the analyst's sample preparation technique. More variation is expected for the relative peak intensities. Identification of the exact crystal form of a drug should be based primarily on observed d spacings with lesser importance placed on relative peak intensities. To identify the anhydrate crystal form of valaciclovir hydrochloride, the fifteen most intense diffraction peaks are reasonably characteristic. These peaks occur at 10.25±0.08, 8.14±0.06, 7.31±0.06, 6.11±0.05, 5.85±0.03, 5.38±0.02, 5.24±0.02, 4.89±0.02, 4.43±0.02, 4.07±0.02, 3.71±0.02, 3.40±0.02, 3.31±0.02, 2.92±0.02, and 2.78±0.02 angstroms. The error in determining d spacings decrease with increasing diffraction scan angle or decreasing d spacing. The error of the 10.25 angstroms peak would be approximately ±0.08 angstrom and the error of the 2.78 angstroms peak would be approximately ±0.01 angstrom for a reasonably aligned diffractometer and reasonably prepared sample.

The first peak in the line listing at 3.56 degrees is due to a hydrated crystal phase of valaciclovir hydrochloride and not due to the anhydrate crystal form.

In a further sample of anhydrous crystalline valaciclovir hydrochloride, the following d spacings were obtained:

10.20, 8.10, 7.27, 6.68, 6.08, 5.83, 5.56, 5.37, 5.23, 5.10, 4.89, 4.42, 4.31, 4.18, 4.06, 3.91, 3.71, 3.64, 3.54, 3.39, 3.35, 3.32, 3.28, 3.22, 3.18, 3.14, 3.08, 3.00, 2.97, 2.91, 2.85, 2.77, 2.70, 2.63, 2.60, 2.55, 2.44, 2.42, 2.37, 2.32.

The fifteen most characteristic peaks are 10.20±0.08, 8.10 ±0.05, 7.27±0.04, 6.08±0.03, 5.83±0.03, 5.37±0.02, 5.23±0.02, 4.89±0.02, 4.42±0.02, 4.06±0.01, 3.71±0.01, 3.39±0.01, 3.32±0.01, 2.9±0.01, and 2.77 +0.01.

EXAMPLE 2

A. 2-[(2-amino-1,6-dihydro-6-oxo-9H-purin-9-yl) methoxyethyl-N-[(benzyloxy)carbonyl]-L-valinate CBZ-L-valine (167 g) was dissolved in dimethylformamide (DMF) (750 ml) and cooled. A cold solution of N,N-dicyclohexyl-carbodiimide (DCC) (153.5 g) in DMF (266 ml) was added followed by acyclovir (111.7 g) in a single portion. 4-(dimethyl-amino)pyridine (9.4 g) was then added and the mixture stirred cold overnight. A white precipitate of the by-product was then removed by filtration. The filtrate was reduced in volume as before to give the title compound (215.3 g).

B. 2-[(2-amino-1,6-dihydro-6-oxo-9H-purin-9-yl) methoxy]ethyl-L-valinate hydrochloride 2-[(2-amino-1,6-dihydro-6-oxo-9H-purin-9-yl)methoxy] ethyl-N-[(benzyloxy)carbonyl]-L-valinate (200 g) was charged to aqueous denatured alcohol (382 ml/908 ml) and heated to reflux to dissolve solids. The solution was then cooled to 40° C. The suspension was treated with a 50% w/w paste of 5% palladium on carbon catalyst and water (40 g) then formic acid (96% w/w: 32.8 ml) added over 1 hour. The reaction mixture was stirred for a further 1 hour then a second charge of formic acid made (20.88 ml) and the mixture filtered to remove the catalyst. The filtrate was treated with concentrated hydrochloric acid (38.56 ml) and the resultant mixture distilled and concentrated under vacuum.

Acetone (1480 ml) was then added over 15 minutes and the suspension stirred for 1 hour before filtering off the product. The solid was then slurried with acetone (ca. 500 ml), refiltered and dried at 60° C. in vacuo to give the title compound (137.75 g: 87.6%).

A 10 g sample of this material was combined with denatured alcohol (3.5 ml), heated at 60° C. for several hours and the solvent then removed in vacuo to afford the product as the desired morphic form.

Result: Valaciclovir hydrochloride in the anhydrous crystalline form was obtained substantially free of other forms of valaciclovir hydrochloride (i.e. in more than about 90% w/w anhydrous crystal form purity).

Physical Data:

The X-ray powder diffraction patterns of the product of example 1B are shown in FIGS. 2 and 3 of the accompanying drawings in which:

FIG. 2 is a linear plot X-ray diffractogram; and

FIG. 3 is a square root plot X-ray diffractogram.

The d spacings and further X-ray diffraction data are shown in Table 2.

TABLE 2

| Peak No: | Angle (degrees) | Peak (counts) | d Spacing pattern (Å) | I/Imax (%) |
|---|---|---|---|---|
| 1 | 3.62 | 2673 | 24.40 | 35 |
| 2 | 7.21 | 119 | 12.26 | 2 |
| 3 | 8.64 | 1910 | 10.22 | 25 |
| 4 | 9.43 | 180 | 9.37 | 2 |
| 5 | 10.86 | 2652 | 8.14 | 35 |
| 6 | 12.12 | 734 | 7.30 | 10 |
| 7 | 13.24 | 615 | 6.68 | 8 |
| 8 | 13.77 | 106 | 6.42 | 1 |
| 9 | 14.50 | 2333 | 6.11 | 31 |
| 10 | 15.14 | 635 | 5.85 | 8 |
| 11 | 15.89 | 511 | 5.57 | 7 |
| 12 | 16.44 | 2652 | 5.39 | 35 |
| 13 | 16.90 | 1267 | 5.24 | 17 |
| 14 | 17.33 | 475 | 5.11 | 6 |
| 15 | 18.13 | 1648 | 4.89 | 22 |
| 16 | 20.05 | 2172 | 4.43 | 28 |
| 17 | 20.56 | 640 | 4.32 | 8 |
| 18 | 21.20 | 1096 | 4.19 | 14 |
| 19 | 21.78 | 2034 | 4.08 | 27 |
| 20 | 21.90 | 1384 | 4.06 | 18 |
| 21 | 22.66 | 729 | 3.92 | 10 |
| 22 | 23.94 | 7621 | 3.71 | 100 |
| 23 | 24.39 | 1624 | 3.65 | 21 |
| 24 | 25.11 | 967 | 3.54 | 13 |
| 25 | 25.86 | 2460 | 3.44 | 32 |
| 26 | 26.21 | 5127 | 3.40 | 67 |
| 27 | 26.82 | 1892 | 3.32 | 25 |
| 28 | 26.89 | 1927 | 3.31 | 25 |
| 29 | 27.19 | 1429 | 3.28 | 19 |
| 30 | 27.99 | 1156 | 3.18 | 15 |
| 31 | 28.35 | 1076 | 3.15 | 14 |
| 32 | 28.87 | 1722 | 3.09 | 23 |
| 33 | 28.94 | 1529 | 3.08 | 20 |
| 34 | 29.62 | 1274 | 3.01 | 17 |
| 35 | 30.56 | 1673 | 2.92 | 22 |
| 36 | 31.30 | 999 | 2.86 | 13 |
| 37 | 32.25 | 2570 | 2.77 | 34 |
| 38 | 33.04 | 1376 | 2.71 | 18 |
| 39 | 34.00 | 1806 | 2.63 | 24 |
| 40 | 34.45 | 1225 | 2.60 | 16 |
| 41 | 35.13 | 1149 | 2.55 | 15 |
| 42 | 36.77 | 1600 | 2.44 | 21 |
| 43 | 38.01 | 576 | 2.37 | 8 |
| 44 | 38.76 | 729 | 2.32 | 10 |
| 45 | 39.52 | 524 | 2.28 | 7 |
| 46 | 40.70 | 751 | 2.22 | 10 |
| 47 | 41.28 | 870 | 2.19 | 11 |
| 48 | 41.88 | 686 | 2.16 | 9 |
| 49 | 42.47 | 718 | 2.13 | 9 |
| 50 | 43.40 | 548 | 2.08 | 7 |
| 51 | 44.53 | 729 | 2.03 | 10 |

The diffraction patterns of the product of example 2B were generated on a Phillips PW1800 Automatic X-ray Powder Diffractometer using a scan of 2 to 45 2Θ with step intervals of 0.02 degrees and an integration time of 4 seconds per step. Generator settings: 40 KV, 45 mA, Cu alpha 1,2 wavelengths: 1.54060, 1.54439 Å; Step size, sample time: 0.020 deg, 4.00 s, 0,005 deg/s; monochromator used: yes; divergence slit: automatic (irradiated sample length: 10.0 mm); peak angle range: 2.000–45.000 deg; range in D spacing: 44.1372–2.01289 Å; peak position criterion: top of smoothed data; cryst peak width range: 0.00–2.00 deg; minimum peak significance: 0.75 maximum intensity: 7621 cts, 1905.3 cps.

The powder sample was prepared as follows:

A 1 gram portion of valaciclovir hydrochloride was transferred to a Retsch 10 ml polystyrol container ref 31-762 containing 2 acrylic balls ref 26-253 and was then ground to a very fine powder using a Retsch MM2 miser mill set at 100% power for five minutes. The ground powder was back loaded into a Philips PW1811/10 sample holder which had been placed inverted on a perfectly smooth surface (e.g. that afforded by a glass plate or a highly polished metal sheet). The powder was then packed into the holder and further powder added and packed until the holder was full. A Philips PW 1811 00 bottom plate was then clamped into the holder and the entire assembly was then inverted before removing the glass/metal plate in an upwards direction to reveal the smooth sample surface which was flush with that of the holder.

As illustrated above, crystalline forms of valaciclovir hydrochloride can be characterised by their X-ray powder diffraction pattern. FIGS. 1 to 3 show diffractograms of the anhydrous crystalline form of valaciclovir hydrochloride as a linear plot (FIGS. 1 and 2) and a square root plot (FIG. 3). In each case the diffractogram displays count rate (intensity of the diffracted peak) against diffraction angle 2Θ. The linear plot allows easy rationing of the peak intensifies whereas the square root plot attenuates small peaks thereby emphasising the main peaks in the diffraction pattern.

EXAMPLE 3

Hyaroscopicity and Stability Measurements of anhydrous Crystalline Valaciclovir Hydrochloride Hygroscopicity: An integrated microbalance system was used to measure equilibrium water sorption profiles (Model MB300G, VTI Corp.), weighing about 20 mg of valaciclovir hydrochloride, and using the following conditions:

Drying parameters:

Temperature: 65° C.; heating rate: 10° C./min; equilibrium criteria: 5 μg; sample interval: 5 min Sorption parameters:

Temperature: 25° C.; equilibrium criteria: 5 μg; sample interval: 5 min.

Data Collection Interval: 2 min

Figure 4:
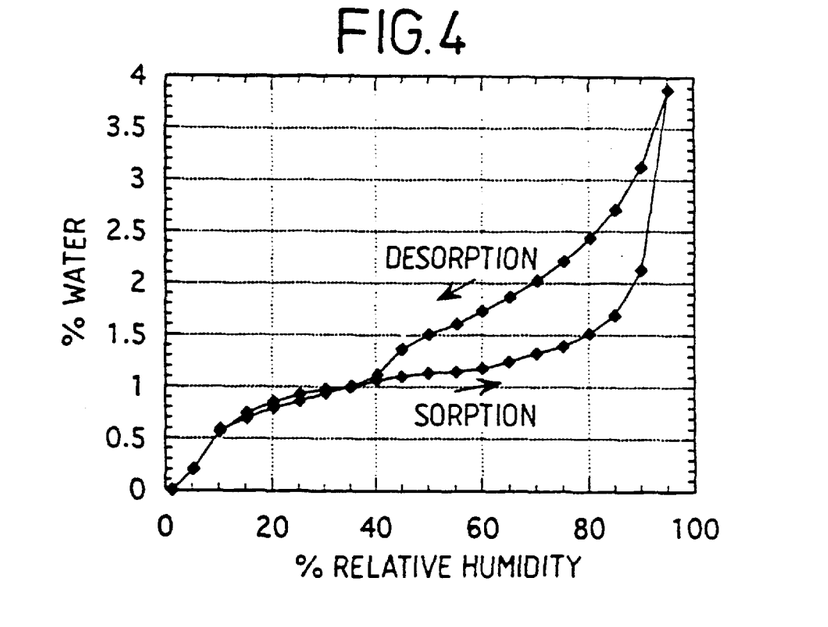

The water sorption/desorption were isotherms noted in FIG. 4.

The isotherm shows that only a small amount of water is absorbed. This absorption is, in fact, due to the presence of hydrated crystal form in the sample which is consistent with the 0.9% w/w water measured by the Karl Fischer titration.

Figure 5:
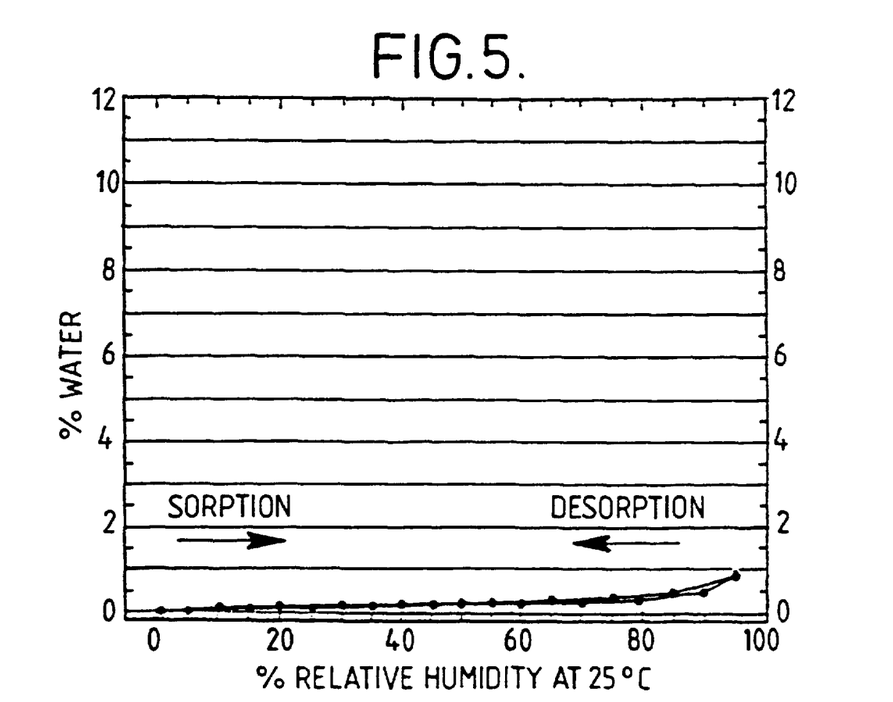

The effect of the small amount of this hydrate can be seen more clearly by comparing with the isotherm of FIG. 5 which was generated with substantially 100% anhydrate crystal form.

X-ray powder diffraction: No change between the initial powder pattern and the patterns of material stored for 4 weeks at 40° C., ambient temp/60% RH (relative humidity), and 40° C./75% RH.

% water:

Initial: 0.9

40° C. 2 weeks: 0.8

40° C. 4 weeks: 0.8
ambient T/60% RH, 2 weeks: 1.0
ambient T/60% RH, 4 weeks: 0.9
40° C./75% RH, 2 weeks: 1.1
40° C./75% RH, 4 weeks: 1.1

Four weeks chemical bulk stability data
% w/w on anhydrous basis

|  | INITIAL | 40° C. | ambient T/60% RH | 40° C./ 75% RH |
|---|---|---|---|---|
| L-valine: | ND (<0.1%) | ND | ND | ND |
| 2-hydroxyethyl valinate hydrochloride: | ND (<0.1%) | ND | ND | ND |
| Acyclovir: | 0.9 | 0.9 | 0.9 | 0.9 |
| Guanine: | ND (<0.1%) | ND | ND | ND |
| D-isomer of valaciclovir; | 1.1 | 1.2* | 1.1 | 1.2* |
| Valaciclovir HCl: | 97.3 | 97.8 | 98.2 | 97.5 |

ND = none detected
Data rounded to nearest 1.1% w/w
*There is no significant increase in 2-hydroxyethyl valinate hydrochloride; the actual values between the initial and 4 week time points are within 0.03% of each other (which is within experimental error).

EXAMPLE 4

Further hygroscopicity and stability studies were carried out on substantially 100% anhydrate crystal form at 30° C./75% RH (12 months) and 40° C./75% RH (6 months).

Samples stored at 30° C./75% RH and 40° C./75% for 12 months and 6 months, respectively, showed no significant change in moisture content (Karl Fischer) or crystallinity (as measured by X-ray powder diffraction). Using the integrated microbalance system, no more than 0.5% w/w water is absorbed at 25° C. at relative humidities of up to 90%. Furthermore, a separate sample stored for 2.5 months at 25° C. and 75% RH corroborated the moisture content measured by the integrated microbalance system, that is, about 0.3% moisture at 75% RH.

The results indicate that the anhydrous crystalline form of valaciclovir hydrochloride is chemically and physically stable.

These characteristics give the anhydrous crystalline form good formulation and storage properties, and assist in obtaining in a highly reproducible manner, batches of high crystalline form purity.

EXAMPLE 5

Tablet Formulation

The following formulations was prepared as follows using anhydrous crystalline valaciclovir.

| Ingredients | Example 5 mg/tablet | w/w | Per Batch (kg) |
|---|---|---|---|
| valaciclovir hydrochloride* | 615 | 65.74 | 5.289 |
| lactose | 205 | 21.91 | 1.763 |
| microcrystalline cellulose (Avicel PH101) (intragranular) | 75 | 8.02 | 0.6450 |
| povidone k30 | 18 | 1.92 | 0.1548 |
| crospovidone (intragranular) | 18 | 1.92 | 0.1548 |
| colloidal silicon dioxide (Aerosil 200) | 0.9 | 0.10 | 0.002598 |
| magnesium stearate | 3.6 | 0.38 | 0.03096 |
| TOTAL WEIGHT | 935.5 | 100 | |

*bulk density 0.45 g/cc after 50 taps (annydrous crystalline form)

EXAMPLE 6

Tablet Formulation

The following formulations was prepared as follows using anhydrous crystalline valaciclovir.

| Ingredients | Example 6 mg/tablet | w/w | Per Batch (kg) |
|---|---|---|---|
| valaciclovir hydrochloride* | 576.5 | 82.3 | 0.9973 |
| crospovidone (intragranular) | 14.0 | 2.0 | 0.02422 |
| povidone k90 (intragranular) | 14.0 | 3.1 | 0.03806 |
| crospovidone (extragranular) | 14.0 | 2.0 | 0.11200 |
| microcrystalline cellulose (Avicel PH101) (extragranular) | 70.0 | 10.0 | 0.05600 |
| colloidal silicon dioxide (CAB-O-SIL M-5 ®) (extragranular) | 2.0 | 0.3 | 0.00160 |
| magnesium stearate (extragranular) | 4.0 | 0.6 | 0.00320 |
| TOTAL WEIGHT | 702.5 | 100.0 | 1.13158 |

*bulk density 0.60 g/cc after 50 taps (anhydrous crystalline form); Karl Fischer water content = 0.4.

TABLET PREPARATION FOR EXAMPLE 5

Step 1. The following ingredients as shown were sifted with a hand screen as shown.

30 Mesh (600 μm) valaciclovir hydrochloride lactose microcrystalline cellulose povidone K30 crospovidone 60 Mesh (250 μm) magnesium stearate colloidal silicon dioxide (CSD)

Step 2. The 30 mesh (600 μm) sifted ingredients from Step 1 were then blended, excluding the povidone, in a 1 cubic foot V-shell blender for 10 minutes.

Step 3. 1.540 kg of SD3A alcohol (ethanol denatured with 5% methanol) was then mixed with 0.6600 kg of purified water and the screened povidone, 0.1548 kg, was dissolved in 0.6192 kg of the mixed solvents by hand stirring.

Step 4. The blended powders from Step 2 were then granulated in a 1 cubic foot Littleford Lodige mixer by adding the dissolved povidone while mixing. 1.315 kg of more mixed solvent was added and the mixture massed for seven minutes total as shown below.

Ploughs 7 min Choppers 6.5 min

Step 5. The granule from Step 4 was then dried in a Fluid Bed Dryer (Glatt GPCG5) with an inlet air temperature of 50° C. to any acceptable moisture content of approximately 1.0 to 3.0% L.O.D.

Step 6. The material from Step 5 was then sifted using a Fitz Mill Model M fitted with a 30 mesh (600 μm) screen, with knives forward, operating at medium speed.

Step 7. The screened a magnesium stearate from Step 1, was added to the material from Step 6 and blended for 5 minutes using the blender from Step 2.

Step 8. Lubricated granule 2.650 kg (from Step 7) was weighed and the sifted CSD, from Step 1, added then dispersed by hand and the mixture blended for 5 minutes in the blender from Step 2. The mixture was compressed to form tablets on a Manesty Beta Press fitted with oval tooling, 19.1 mm×10.2 mm, at a compression weight of approximately 935.5 mg.

Tablet Preparation For Example 6

Step 1. The core ingredients were sifted with a 20 mesh (850 μm) hand screen, and then blended in an appropriately sized V-shell blender for 10 minutes.

Step 2. The blended powders from Step 1 were then granulated in a 10 litre high shear mixer (model-SP1) by adding pure water while mixing. Approximately 11–14% water, w/w of the core ingredients was then added and the mixture massed for 3 to 4½ minutes.

Step 3. The granule from Step 2 was dried in a tray (examples 5, 6 and 7) or vacuum (examples 3 and 4) drier (model-SP1) at a temperature of 50° C. to an acceptable moisture content of approximately 1.0 to 2.0% L.O.D.

Step 4. The remaining ingredients were sifted through a 20 mesh screen and added to the core ingredients of step 3, and then the mixture was sifted using a Comil Model 197 AS fitted with a 0.062" screen.

Step 5. The mixture was then blended in an appropriately sized V-shell blender for 5 minutes.

Step 6 The blended granule from Step 5 was compressed on a Manesty Beta Press fitted with capsule shaped tooling, 18.25 mm×7.14 mm, at a compression weight of approximately 700 mg and a compression force of about 14.5 to 18 kN.

Step 7 the tablet can then optionally be film coated using standard methods such as using white colour concentrate, methylhydroxypropykellulose, titanium dioxide, polyethylene glycol and polysorbate.

What is claimed is:

1. Storage stable Valaciclovir hydrochloride in anhydrous crystalline form and being essentially free of water of hydration including the following d spacing pattern (in Angstroms): 10.20±0.08, 8.10±0.06, 7.27±0.06, 6.08±0.05, 5.83±0.03, 5.37±0.02, 5.23±0.02, 4.89±0.02, 4.42±0.02, 4.06±0.02, 3.71±0.02, 3.39±0.02, 3.32±0.02, 2.91±0.02, 2.77±0.02.

2. Crystalline valaciclovir hydrochloride as claimed in claim 1 having a water of hydration content of not more than 3% w/w.

3. Crystalline valaciclovir hydrochloride as claimed in claim 2 having a water of hydration content of not more than 2% w/w.

4. Crystalline valaciclovir hydrochloride as claimed in claim 3 having a water of hydration content of riot more than 1% w/w.

5. A method for the treatment of herpes viral infection in a human which comprises administering to the human host, an effective anti-herpes viral amount of storage stable valaciclovir hydrochloride in anhydrous crystalline form and being essentially free of water of hydration as claimed in claim 1.

6. A process for the production of storage stable valaciclovir hydrochloride in anhydrous crystalline form and being essentially free of water of hydration including the d spacings as defined in claim 1, said process comprising treating valaciclovir hydrochloride with an amount of 15% to 40% w/w lower alcohol having 1 to 4 carbon atoms or a lower ketone containing from 3 to 6 carbon atoms serving to convert an amount of said valaciclovir hydrochloride into said anhydrous crystalline form; and then isolating said anhydrous crystalline form.

7. A process for the production of storage stable valaciclovir hydrochloride in an anhydrous crystalline form and being essentially free of water of hydration including the d spacings as defined in claim 1, said process comprising the steps of:

a) forming valaciclovir in solution either in free base or salt form;

b) converting said free base valaciclovir or salt thereof to valaciclovir hydrochloride;

c) isolating valaciclovir hydrochloride from the solution and optionally removing unbound solvent leaving the valaciclovir hydrochloride in substantially dry form;

d) treating valaciclovir hydrochloride with 15% to 40% w/w of a lower alcohol having 1 to 4 carbon atoms or a lower ketone containing from 3 to 6 carbon atoms serving to convert an amount of said optionally dried valaciclovir hydrochloride into said anhydrous crystalline form; and e) isolating said anhydrous crystalline form.

8. A process as claimed in claim 7 wherein the lower alcohol is ethanol or a solvent composed substantially of ethanol.

9. A process as claimed in claim 8 wherein the lower alcohol is ethanol or a solvent composed substantially of ethanol and is added in a range of about 17% by weight to about 40% by weight of substantially dry valaciclovir hydrochloride.

* * * * *